United States Patent
Wognum et al.

(10) Patent No.: US 7,135,340 B2
(45) Date of Patent: Nov. 14, 2006

(54) TETRAMERIC ANTIBODY COMPLEXES FOR BLOCKING NON-SPECIFIC LABELING OF ANTIGENS

(75) Inventors: Albertus Wernerus Wognum, Vancouver (CA); Peter Michael Lansdorp, Vancouver (CA)

(73) Assignee: Stemcell Technologies Inc., Vancouver (CA)

( * ) Notice: Subject to any disclaimer, the term of this patent is extended or adjusted under 35 U.S.C. 154(b) by 680 days.

(21) Appl. No.: 10/289,213

(22) Filed: Nov. 7, 2002

(65) Prior Publication Data

US 2003/0119071 A1    Jun. 26, 2003

Related U.S. Application Data

(60) Provisional application No. 60/331,060, filed on Nov. 7, 2001.

(51) Int. Cl.
G01N 33/53    (2006.01)
(52) U.S. Cl. .................. 435/962; 435/7.1; 435/7.92; 436/819; 436/825; 436/501
(58) Field of Classification Search .............. 435/7.1, 435/7.92, 962, 972; 436/501, 819, 825, 540, 436/548, 175
See application file for complete search history.

(56) References Cited

U.S. PATENT DOCUMENTS 4,810,635 A * 3/1989 Ledden et al. ............... 435/7.7
4,868,109 A   9/1989 Lansdorp
2002/0150561 A1 * 10/2002 Kraus et al. ................. 424/93.7
2003/0077576 A1 * 4/2003 Trial et al. ...................... 435/5

OTHER PUBLICATIONS

Wognum et al., An Enzme-Linked Immunosorbent Assay for Erythropoietin Using Monoclonal Antibodies, Tetrameric Immune Complexes, and Substrate Amplification, Blood, vol. 74, No. 2 1989: pp. 622-628.*

Lansdorp et al., Cyclic tetramolecular complexes of monoclonal antibodies: a new type of cross-linking reagent, European Journal of Immunology, (1986) vol. 16, No. 6, pp. 679-683.*

Wognum, A.W. et al. "Use of Tetrameric Antibody Complexes to Stain Cells For Flow Cytometry", Cytometry 8:366-371 (1987).

Wognum, A.W. et al., "Flow Cytometric Detection of Receptors For Interleukin-8 on Bone Marrow and Peripheral Blood Cells of Humans and Rhesus Monkeys", Blood, vol. 61, No. 8, pp. 2036-2043 (1993).

* cited by examiner

*Primary Examiner*—Long V. Le
*Assistant Examiner*—Gary W. Counts
(74) *Attorney, Agent, or Firm*—Bereskin & Parr; Micheline Gravelle

(57) ABSTRACT

A method for preventing or inhibiting non-specific binding reactions between a detection reagent and an antigen in an immunological assay is described. The method involves using tetrameric antibody complexes that can bind to the antigen and are comprised of two monoclonal antibodies of a first animal species linked to two monoclonal antibodies of a second animal species that can bind the antibodies of the first animal species. Preferably, the antigen is an Fc Receptor and the method reduces the binding of a detection antibody with Fc receptors present on the surface of many cells.

5 Claims, No Drawings

TETRAMERIC ANTIBODY COMPLEXES FOR BLOCKING NON-SPECIFIC LABELING OF ANTIGENS

This application claims the benefit under 35 USC §119(e) from U.S. provisional patent application Ser. No. 60/331,060, filed Nov. 7, 2001.

FIELD OF THE INVENTION

The present invention relates to methods for reducing or inhibiting the non-specific binding of a detection reagent to an antigen in an immunological assay.

BACKGROUND OF THE INVENTION

Non-specific staining is a major problem in immunological determinations, which measure the presence of an antigen on cells or in solutions or which isolate specific cells or proteins on the basis of binding of detection reagents that specifically recognize these antigens. The specific binding of a detection reagent to its target antigen cannot be distinguished from non-specific binding to other structures that are unrelated to the antigen of interest. Ideally, detection reagents used in immunological determinations specifically recognize the antigens of interest, but do not bind to other unrelated molecules on the same test cells or in the same test solution. Monoclonal antibodies raised against the antigen of interest are used most often, but not exclusively, as detection reagents. Polyclonal antibodies or non-immunoglobulin reagents, e.g., cytokines or synthetic antibody-like molecules are used as well, but less frequently.

A major, but not the only, source of non-specific signals in immunological determinations is the interaction of antibodies with Fc-receptors (FcR) on the surface of various blood cells or present in soluble form in blood serum and plasma. Examples of FcR expressing cells are monocytes/macrophages, NK cells, B cells, and platelets. Examples of Fc Receptors that can bind antibodies or antibody complexes are CD16, CD23, CD32, and CD69 Antibody/FcR interactions are mediated through the constant or Fc part of the molecule. The Fc part is also involved in other non-specific antibody interactions which are not mediated through Fc receptors. Removal of the Fc part of antibodies by chemical or enzymatic protein digestion can effectively remove FcR mediated or other non-specific interactions. Disadvantages of these approaches are that the chemical or enzymatic procedures that remove the Fc part of antibodies can damage the antibody molecule and decrease its stability and performance. Digestion conditions need to be carefully optimized for each individual antibody preparation to achieve minimal damage and maximal recovery. This increases the amount of labour and cost involved. The removal of the Fc region may also reduce detection sensitivity. The reason is that the smaller size of the digested antibodies reduces the amount of fluorochrome, enzyme or other label that can be effectively attached to the detection antibody without inhibiting or eliminating its antigen binding ability.

Desirable approaches to prevent non-specific binding of detection antibodies in immunological determinations prevent FcR and other non-specific interactions by non-modified, intact detection antibodies and can be applied generically without need for optimization for different applications and assay formats.

SUMMARY OF THE INVENTION

The present invention relates to the use of tetrameric antibody complexes in a method to reduce or inhibit the non-specific binding of a detection reagent to an antigen in a sample. The tetrameric antibody complex comprises two monoclonal antibodies of a first animal species linked to two monoclonal antibodies of a second animal species that can bind the antibodies of the first animal species. The tetrameric antibody complex binds to the antigen responsible for non-specific binding. In particular, the inventors have shown that blocking of the Fc receptor CD32 on monocytes using tetrameric antibody complexes where the monoclonal antibody of the first animal species recognizes CD32 reduces monocyte contamination of purified lymphocyte subsets that are isolated in an immunological assay using test or diagnostic antibodies and cell separation experiments. The inventors have further shown that the anti-CD32 tetrameric antibody complex is much more efficient than using anti-CD32 antibodies alone.

Accordingly, the present invention provides a method of reducing or inhibiting the non-specific binding of a detection reagent to an antigen in a sample comprising contacting the sample with a tetrameric antibody complex that can bind to the antigen comprising (a) two monoclonal antibodies of a first animal species and (b) two monoclonal antibodies of a second animal species that can bind to the antibodies of the first animal species.

The present invention also provides a method for reducing or inhibiting the non-specific binding of a detection reagent to a first antigen in a sample comprising:

(1) contacting the sample with a tetrameric antibody complex that can bind to the first antigen comprising:
   (a) two antibodies of a first animal species; and
   (b) two antibodies of a second animal species that bind to the antibodies of the first animal species;
(2) contacting the sample with the detection reagent that specifically binds to a second antigen in the sample and non-specifically binds to the first antigen;
(3) allowing conjugates to form between the detection reagent and the second antigen and the tetrameric antibody complex and the first antigen; and
(4) optionally removing the conjugates between the detection reagent and the second antigen and/or the conjugates between the tetrameric antibody complex and the first antigen.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

As hereinbefore mentioned, the present inventors have demonstrated that tetrameric antibodies are very efficient for blocking the non-specific binding of a detection reagent to an antigen in a sample. Accordingly, the present invention provides a method of reducing or inhibiting the non-specific binding of a detection reagent to an antigen in a sample comprising contacting the sample with a tetrameric antibody complex, wherein the tetrameric antibody complex comprises (a) two monoclonal antibodies of a first animal species and (b) two monoclonal antibodies of a second animal species that can bind to the antibodies of the first animal species.

The term "antigen" as used herein includes any molecule to which an antibody or tetrameric antibody complex can bind, either specifically or non-specifically. In the above assay, the antigen is the molecule to which you want to reduce non-specific binding by the detection reagent.

The term "specific binding" means that the antibody has been generated to specifically bind to the antigen and binds to the antigen through its variable region. As an example, an antibody to CD32, specifically binds to the antigen CD32.

The term "non-specific binding" means that the antibody has not been generated to specifically bind to the antigen but does somehow bind the antigen through non-specific means. As one example, an antibody will non-specifically bind to an Fc receptor through the Fc portion of the antibody molecule. As another example, certain antibodies may inadvertently cross-react with antigens to which they were not generated.

The term "detection reagent" includes any reagent that one would use in an immunological determination or assay. In the assay of the invention, the detection reagent will be capable of binding to the antigen in a non-specific manner. The detection reagent can be an immunoglobin molecule including both monoclonal or polyclonal antibodies or a non-immunoglobin molecule such as a cytokine. Preferably the detection reagent is an antibody. When the detection reagent is an antibody it will bind to the antigen in a non-specific manner such as through the binding of its Fc portion to an FcR.

In one embodiment, the antigen to which one wants to reduce non-specific binding is a cell surface antigen such as an Fc receptor (FcR). FcRs are one of the major sources of non-specific binding in immunological determinations when the detection reagent is an antibody as antibodies will bind the FcRs (that are on the surface of various blood cells or present in soluble form) through their Fc portion. Examples of FcRs that can bind antibodies or antibody complexes are CD16, CD23, CD32 and CD69. In a specific embodiment, the FcR is CD32.

The tetrameric antibody complex will be capable of binding to the antigen either specifically or non-specifically. In non-specific binding, one or more antibodies in the complex may bind the antigen through their Fc portion or through other non-specific means. In the non-specific binding situation, any type of antibody can be used in the tetrameric complex as the antigen-specificity is not important. This is demonstrated in Examples 3 and 4. In specific binding, one or more antibodies in the complex will have specificity for the antigen through their variable regions. This is demonstrated in Example 2.

In one embodiment, in the tetrameric antibody complex, at least one of the antibodies of the first animal species specifically binds to the antigen. In a preferred embodiment, both of the antibodies of the first animal species specifically bind to the antigen. More preferably, the antibodies of the first animal species are specific for a surface antigen including an Fc receptor such as CD16, CD23, CD32 and CD69. Most preferably, the antibodies are specific for CD32. Preferably, the first animal species is a mouse. Examples of murine monoclonal antibodies against human FcRs that can be used in the present invention are shown in Table 1.

The two antibodies of a second animal species can be any antibodies that can bind specifically to the antibodies of the first animal species. For example, when the first animal species is a mouse, then the two antibodies of the second animal species will bind to mouse antibodies. Preferably, the two antibodies of the second animal species are from rat. In a specific embodiment, the antibodies of the second animal species are rat antibodies that bind to murine IgG1.

Within the context of the present invention, antibodies are understood to include monoclonal antibodies. Monoclonal antibodies specific for selected antigens on the surface of cells may be readily generated using conventional techniques (see U.S. Pat. Nos. RE 32,011, 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference).

Other techniques may also be utilized to construct monoclonal antibodies (see William D. Huse et al., "Generation of a Large Combinational Library of the Immunoglobulin Repertoire in Phage Lambda," *Science* 246:1275–1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," *Proc Natl. Acad. Sci USA* 86:5728–5732, August 1989; see also Michelle Alting-Mees et al., "Monoclonal Antibody Expression Libraries: A Rapid Alternative to Hybridomas," Strategies in Molecular Biology 3:1–9, January 1990; these references describe a commercial system available from Stratacyte, La Jolla, Calif. which enables the production of antibodies through recombinant techniques).

Similarly, binding partners may be constructed utilizing recombinant DNA techniques. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. The primers may be utilized to amplify heavy or light chain variable regions, which may then be inserted into vectors such as ImmunoZAP™ H or ImmunoZAP™ L (Stratacyte), respectively. These vectors may then be introduced into *E. coli* for expression. Utilizing these techniques, large amounts of a single-chain protein containing a fusion of the $V_H$ and $V_L$ domains may be produced (See Bird et al., Science 242:423–426, 1988). In addition, such techniques may be utilized to change a "murine" antibody to a "human" antibody, without altering the binding specificity of the antibody.

Antibodies against selected antigens on the surface of cells may also be obtained from commercial sources.

A tetrameric immunological complex may be prepared by mixing monoclonal antibodies from a first animal species with an about equimolar amount of monoclonal antibodies of a second animal species which are directed against the Fc-fragments of the antibodies of the first animal species. The antibodies of the first animal species may also be reacted with an about equimolar amount of the $F(ab')_2$ fragments of monoclonal antibodies of a second animal species which are directed against the Fc-fragments of the antibodies of the first animal species. (See U.S. Pat. No. 4,868,109 to Lansdorp, which is incorporated herein by reference for a description of tetrameric antibody complexes and methods for preparing same).

In a specific embodiment, the present invention provides a method for reducing or inhibiting the non-specific binding of a detection reagent to a first antigen in a sample comprising:
(1) contacting the sample with a tetrameric antibody complex that binds to the first antigen comprising:
   (a) two antibodies of a first animal species; and
   (b) two antibodies of a second animal species that bind to the antibodies of the first animal species;
(2) contacting the sample with the detection reagent that specifically binds to a second antigen in the sample and non-specifically binds to the first antigen;
(3) allowing conjugates to form between the detection reagent and the second antigen and the tetrameric antibody complex and the first antigen; and
(4) optionally removing the conjugates between the detection reagent and the second antigen and/or the conjugates between the tetrameric antibody complex and the first antigen.

The detection reagent is preferably an antibody and the second antigen is a cell surface antigen. The method can be either a positive or negative selection protocol. In the former, the second antigen is present on the cells that you wish to enrich from the sample. In the latter, the second antigen will be present on the undesired cells that you wish to remove from the sample. In a preferred embodiment, the detection antibody is in a tetrameric antibody complex as described in Example 2.

In such an embodiment, the conjugates between the detection antibody and the second antigen are removed by magnetic separation using magnetic particles as described in Example 2. Suitable magnetic particles include particles in ferrofluids and other colloidal magnetic solutions. "Ferrofluid" refers to a colloidal solution containing particles consisting of a magnetic core, such as magnetite ($Fe_3O_4$) coated or embedded in material that prevents the crystals from interacting. Examples of such materials include proteins, such as ferritin, polysaccharides, such as dextrans, or synthetic polymers such as sulfonated polystyrene cross-linked with divinylbenzene. The core portion is generally too small to hold a permanent magnetic field. The ferrofluids become magnetized when placed in a magnetic field. Examples of ferrofluids and methods for preparing them are described by Kemshead J. T. (1992) In J. Hematotherapy, 1:35–44, at pages 36 to 39, and Ziolo et al. Science (1994) 257:219 which are incorporated herein by reference. Colloidal particles of dextran-iron complex are preferably used in the process of the invention. (See Molday. R. S. and McKenzie, L. L. FEBS Left. 170:232, 1984; Miltenyi et ml., Cytometry 11:231, 1990; and Molday, R. S. and Mackenzie, D., J. Immunol. Methods 52:353, 1982; Thomas et ml., J. Hematother. 2:297 (1993); and U.S. Pat. No. 4,452,773 which are each incorporated herein by reference).

In accordance with the magnetic separation method, the sample containing the detection reagent and cells containing the second antigen that binds to the detection reagent is reacted with tetrameric antibody complexes. The reaction conditions are selected to provide the desired level of binding of the targeted cells and the detection reagents. Preferably the sample is incubated with the antibody reagents for a period of 5 to 60 minutes at either 4° C. or ambient room temperature. The concentration of the antibody reagents is selected to optimize cell labeling in a sample of $2-8 \times 10^7$ nucleated cells per ml. Generally, the concentration is between about 0.1 to 50 µg/ml of sample. The magnetic particles are then added and the mixture is incubated for a period of about 5 minutes to 30 minutes at the selected temperature. The sample is then ready to be separated over a magnetic filter device. Preferably, the magnetic separation procedure is carried out using the magnetic filter and methods described in co-pending U.S. Pat. No. 5,514,340 to Lansdorp and Thomas which is incorporated in its entirety herein by reference.

The sample containing the magnetically labelled cell conjugates is passed through the magnetic filter in the presence of a magnetic field. In a preferred embodiment of the invention, the magnet is a permanent gap magnet with 0.5–2.0" diameter bore and having a magnetic field of 0.5–2 Tesla. The magnetically labelled cell conjugates are retained in the high gradient magnetic column and the materials which are not magnetically labelled flow through the column after washing with a buffer.

The following non-limiting examples are illustrative of the present invention.

EXAMPLES

Example 1

Preparation of Anti-CD32/Anti-CD32 Tetrameric Antibody Complexes.

To generate tetrameric complexes, an amount of anti-CD32 monoclonal antibody (clone 7.30) diluted in phosphate buffered saline (PBS) was mixed with an equimolar amount of rat monoclonal antibodies against mouse $IgG_1$ (clone P9). The mixture was incubated for 16 hours at 37 degrees Celsius and then stored at 4 degrees Celsius until use.

Example 2

Blocking of the Fc Receptor CD32 on Monocytes by Anti-CD32/Anti-CD32 Tetrameric Antibody Complexes Reduces Monocyte Contamination of Purified Lymphocyte Subsets Isolated by Immunomagnetic Separation.

The ability of anti-CD32/anti-CD32 tetrameric antibody complexes (TAC) to block non-specific binding of antibodies was tested in cell separation experiments. B-lymphocytes were positively selected from peripheral blood mononuclear cells by sequential binding to anti-CD19/anti-dextran TAC and magnetic dextran-coated colloid, followed by passage over a column in a magnetic field. The positively selected cells were recovered after washing of the column and release of the bound cells after removal of the column from the magnetic field. In the absence of anti-CD32 antibodies the purity of B-lymphocytes was only 93% and close to 6% of recovered cells consisted of monocytes (Table 2). Similar results were obtained with cells that had been pre-incubated with anti-CD32 antibodies, but B cell purity was increased to 96% and monocyte contamination was reduced 3-fold to 1.6% if cells were pre-incubated with anti-CD32/anti-CD32 TAC. This demonstrates that anti-CD32 antibodies alone are not effective in reducing non-specific interaction of monocytes with the anti-CD19/anti-dextran complexes used for cell separation, but that the binding of the same anti-CD32 antibody in tetrameric antibody complexes enhances the ability of the antibody to block the non-specific binding of monocytes. The blocking ability of the anti-CD32/anti-CD32 TAC was directly compared with the blocking ability of a tetrameric antibody complex prepared with a mouse $IgG_1$ antibody directed against an antigen not expressed on the cells (anti-peroxidase) instead of anti-CD32 (Table 3).

The anti-peroxidase TAC's were also able to reduce non-specific binding of monocytes but the anti-CD32/anti-CD32 TACs were more effective.

Example 3

Blocking of Non-specific Staining of Fluorescently Labelled Antibodies to Human Blood Cells by Tetrameric Antibody Complexes Against Antigens Other than Fc Receptors.

Human peripheral blood mononuclear cells were contacted with a fluorescein-labelled antibody against the cell-surface antigen CD19, which is a marker on B-lymphocytes. Binding of the labelled antibody to cells was detected by flow cytometry. In addition to B-lymphocytes, which express CD19 and bind the anti-CD19 antibody specifically, the labelled anti-CD19 antibody bound non-specifically to monocytes, which do not express CD19. Pre-incubation of the cells with a tetrameric antibody complex comprised of a mouse monoclonal antibody against CD19 and a mouse monoclonal antibody against dextran, held together by two rat monoclonal antibodies against mouse $IgG_1$, prevented the non-specific binding of the fluorescein-labelled antibody to monocytes. The specific binding of the fluorescein-labelled antibody to B-lymphocytes was not prevented by the tetrameric complex, since different anti-CD19 clones, directed against different epitopes on CD19 were used for the fluorescein-labelled antibody and the tetrameric complex.

In a similar approach non-specific binding of fluorescein-labelled anti-CD8 antibodies to monocytes, but not the specific binding to CD8+ T-lymphocytes, was prevented by pre-incubation of human peripheral blood mononuclear with an anti-CD8/anti-dextran tetrameric antibody complex. These results demonstrate that the ability of tetrameric antibody complexes to block non-specific binding of antibodies to monocytes is not restricted to the use of antibodies against Fc Receptors.

Example 4

Blocking of Non-specific Staining of Fluorescently Labelled Antibodies to Human Blood Cells by Tetrameric Antibody Complexes Against Antigens Other than Fc Receptors.

Human peripheral blood mononuclear cells were contacted with a fluorescein-labelled antibody against the cell-surface antigen CD3, which is a marker on T-lymphocytes. Binding of the labelled antibody to cells was detected by flow cytometry. In addition to T-lymphocytes, which express CD3 and bind the anti-CD3 antibody specifically, the labelled anti-CD3 antibody bound non-specifically to monocytes, which do not express CD3. Pre-incubation of the cells with a tetrameric antibody complex comprised of mouse monoclonal antibodies against dextran, held together by two rat monoclonal antibodies against mouse $IgG_1$, prevented the non-specific binding of the fluorescein-labelled antibody to monocytes.

As in Example 3, these results demonstrate that the ability of tetrameric antibody complexes to block non-specific binding of antibodies to monocytes is not restricted to the use of antibodies against Fc Receptors.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Examples of mouse monoclonal antibodies against human Fc-receptors

| Antigen | Clone | Subclass | Supplier |
|---|---|---|---|
| CD16 | NKP-15 | $IgG_1$ | BD/Pharmingen, Mountain View, CA |
| CD16 | B73.1 | $IgG_1$ | BD/Pharmingen, Mountain View, CA |
| CD16 | 3G8 | $IgG_1$ | Immunotech, Marseille, France |
| CD23 | EBVCS-5 | $IgG_1$ | BD/Pharmingen, Mountain View, CA |
| CD32 | IV3 | $IgG_1$ | Medarex, Princeton, NJ |
| CD32 | 7.30 | $IgG_1$ | StemCell Technologies Inc, Vancouver, Canada |
| CD32 | FL18.26 (2003) | $IgG_1$ | BD/Pharmingen, Mountain View, CA |
| CD32 | C1KM5 | $IgG_1$ | Caltag, Burlingame; CA |
| CD32 | KB61 | $IgG_1$ | DAKO, Copenhagen, Denmark |
| CD69 | L78 | $IgG_1$ | BD/Pharmingen, Mountain View, CA |

TABLE 2

Frequency of target cells (CD20+ B-lymphocytes) and contaminating monocytes after B cell isolation from human peripheral blood in the absence and presence of anti-CD32 antibody or anti-CD32/anti-CD32 tetrameric antibody complexes (TAC).

| Blocking reagent | Target cell purity % | Contaminating monocytes (%) |
|---|---|---|
| None | 93 | 5.8 |
| anti-CD32 clone 7.30 | 93 | 5.9 |
| Anti-CD32/anti-CD32 TAC | 96 | 1.6 |

TABLE 3

Frequency of target cells (CD20+ B-lymphocytes) and contaminating monocytes after B cell isolation from human peripheral blood in the absence and presence of anti-CD32/anti-CD32 tetrameric antibody complexes (TAC) or tetrameric complexes (TAC) made with a mouse $IgG_1$ monoclonal antibody against horse radish peroxidase (anti-HRP).

| Blocking reagent | Target cell purity (%) | Contaminating monocytes (%) |
|---|---|---|
| None | 67 | 29.2 |
| Anti-CD32/anti-CD32 TAC | 93 | 4.5 |
| Anti-HRP/anti-HRP TAC | 87 | 9.1 |

We claim:

1. A method of reducing or inhibiting the non-specific binding of a detection reagent to an antigen in a sample comprising
    (i) contacting the sample with a tetrameric antibody complex specific for the antigen, wherein the tetrameric antibody complex comprises (a) two monoclonal antibodies of a first animal species and (b) two monoclonal antibodies of a second animal species that can bind to the antibodies of the first animal species and wherein born the monoclonal antibodies of the first animal species bind to the antigen; and (ii) contacting the sample with the detection reagent which can bind non-specifically to the antigen, wherein the binding of the tetrameric complex to the antigen reduces or inhibits the non-specific binding of the detection reagent to the antigen in the sample.

2. The method according to claim 1 wherein the antigen is a cell-surface antigen.

3. The method of claim 1 wherein the antigen is on monocytes.

4. The method according to claim 2 wherein the cell-surface antigen is an Fc receptor.

5. The method according to claim 4 wherein the Fc receptor is CD32, CD16, CD23 or CD69.

* * * * *

UNITED STATES PATENT AND TRADEMARK OFFICE
CERTIFICATE OF CORRECTION

| | |
|---|---|
| PATENT NO. | : 7,135,340 B2 |
| APPLICATION NO. | : 10/289213 |
| DATED | : November 14, 2006 |
| INVENTOR(S) | : Albertus Wernerus Wognum and Peter Michael Landsorp |

It is certified that error appears in the above-identified patent and that said Letters Patent is hereby corrected as shown below:

On the cover page, "Other Publications" section, first line, replace "Enzme-Linked" with --Enzyme-Linked--;

Column 8, line 18, Table 1, replace "$IgG_1$" under the Subclass for Antigen CD32, Clone IV3 with --$IgG_{2b}$--;

Column 8, line 20, Table 1, replace "IgG1" under the Subclass for Antigen CD32, Clone FL18.26 (2003) with --$IgG_{2b}$--;

Column 9, line 1, replace "born" with --both--.

Signed and Sealed this

Fourth Day of September, 2007

JON W. DUDAS
*Director of the United States Patent and Trademark Office*